US006613288B2

(12) United States Patent
Gupte

(10) Patent No.: US 6,613,288 B2
(45) Date of Patent: Sep. 2, 2003

(54) DEVICE FOR RELEASING A VOLATILE MEDIUM

(75) Inventor: Anil J. Gupte, St. Charles, IL (US)

(73) Assignee: Candle Corporation of America, Elkin, NC (US)

( * ) Notice: Subject to any disclaimer, the term of this patent is extended or adjusted under 35 U.S.C. 154(b) by 0 days.

(21) Appl. No.: 09/766,761

(22) Filed: Jan. 22, 2001

(65) Prior Publication Data

US 2002/0098140 A1 Jul. 25, 2002

(51) Int. Cl.[7] .............................. A62B 7/08; A61L 9/00; G02B 27/00; F24J 2/02; F24J 2/08
(52) U.S. Cl. .................. 422/125; 422/306; 126/680; 126/699; 126/700; 359/810
(58) Field of Search ................... 422/1, 120, 244, 422/285, 288–293, 300, 305–307, 311, 900; 126/680–681, 698–700; 359/810

(56) References Cited

U.S. PATENT DOCUMENTS

| 612,675 A | 10/1898 | Rieke |
| 1,535,486 A | 4/1925 | Lundy |
| 1,960,098 A | 5/1934 | Breitenbach .................... 167/3 |
| 2,001,672 A | 5/1935 | Carpenter ..................... 201/63 |
| 2,254,906 A | 9/1941 | Petrulis ........................ 21/117 |
| 2,451,238 A | 10/1948 | Pritchard ..................... 21/117 |
| 2,462,952 A | 3/1949 | Dunkak ....................... 183/4.5 |
| 2,687,126 A | 8/1954 | Bouchet ....................... 126/270 |
| 3,080,624 A | 3/1963 | Weber III ..................... 21/120 |
| 3,118,437 A | 1/1964 | Hunt ............................ 126/270 |
| 3,182,654 A | 5/1965 | Culling ........................ 126/270 |
| 3,767,910 A | 10/1973 | Harrigan ..................... 240/10 B |
| 3,773,460 A | 11/1973 | Tellier ........................ 431/289 |
| 3,780,722 A | 12/1973 | Swet ............................ 126/270 |
| 3,817,605 A | 6/1974 | Franklin et al. ............. 350/294 |
| 3,948,445 A | 4/1976 | Andeweg ..................... 239/53 |
| 4,009,384 A | 2/1977 | Holland .................. 240/108 R |
| 4,070,861 A | 1/1978 | Scragg et al. ................. 60/641 |
| 4,076,014 A | 2/1978 | Wiquel ........................ 126/270 |
| 4,142,512 A | 3/1979 | Brown ........................ 126/271 |
| 4,254,761 A | 3/1981 | Armas et al. ................ 126/451 |
| 4,267,824 A | 5/1981 | O'Halloran .................. 126/426 |
| 4,316,451 A | 2/1982 | Hicks .......................... 126/440 |
| 4,332,663 A | 6/1982 | Berneke ...................... 204/277 |
| 4,346,059 A | 8/1982 | Spector ....................... 422/125 |
| 4,568,521 A | 2/1986 | Spector ....................... 422/124 |
| 4,610,240 A | 9/1986 | Burch ......................... 126/440 |
| 4,666,638 A | 5/1987 | Baker et al. .................. 261/26 |
| 4,695,435 A | 9/1987 | Spector ....................... 422/124 |
| 4,781,895 A | 11/1988 | Spector ....................... 422/125 |
| 4,849,181 A | * 7/1989 | Kelley et al. |
| 4,892,711 A | 1/1990 | Tendick, Sr. ................. 422/125 |
| 4,893,612 A | * 1/1990 | Dawson |
| 5,250,265 A | 10/1993 | Kawaguchi et al. ......... 422/107 |
| 5,433,595 A | 7/1995 | Wentzell et al. ............. 431/289 |
| 5,927,272 A | 7/1999 | Robertson .................... 126/699 |
| 6,033,212 A | 3/2000 | Bonnema et al. ........... 431/344 |

FOREIGN PATENT DOCUMENTS

| EP | 0 328 370 A2 | 8/1989 | |
| FR | 2 286 344 | 4/1976 | |
| FR | 2 438 232 | 4/1980 | |
| JP | 0 338 555 | * 10/1989 | .............. F24J/2/02 |
| WO | WO 90/05881 | * 5/1990 | .............. F24J/2/08 |

OTHER PUBLICATIONS

European Search Report, dated May 16, 2002, Application No. PCT/US 02/01825.

* cited by examiner

Primary Examiner—Robert J. Warden, Sr.
Assistant Examiner—Monzer R. Chorbaji
(74) Attorney, Agent, or Firm—Marshall, Gerstein & Borun

(57) ABSTRACT

An apparatus for heating a volatile medium is provided. The apparatus of the invention includes a base and a rotatable lens positioned above the base. The rotatable lens rotates independently of the base in the direction of a light source. The lens is positioned such that a focal point of a lens is focused on the volatile medium. The heat generated by focusing the light in this manner vaporizes the volatile medium and releases the medium into the surrounding atmosphere in a continuous manner.

31 Claims, 3 Drawing Sheets

DEVICE FOR RELEASING A VOLATILE MEDIUM

BACKGROUND OF THE INVENTION

1. Field of the Invention

The invention is directed generally to devices for holding a volatile medium. More specifically, the invention is directed to a matchless device for heating a fragrance material or other volatile medium.

2. Description of Related Technology

Fragrance materials have become increasingly popular as an aesthetic complement to the home. They can be used both indoors and outdoors to freshen the surrounding air with an aesthetic scent or simply as decoration. However, heat needs to be applied in order to use the fragrance material. For example, fragrance materials release their fragrance more intensely when heat is applied. The heat vaporizes a volatile fragrance medium, usually a liquid, entrapped in a solid or on a solid material, thus releasing the fragrance vapor into the surrounding atmosphere and carrying with it the aesthetic scent.

Past devices and method for heating a fragrance material include using a flame. Matches and butane lighters must generally be used to at least start the flame. Often this can lead to burnt fingers or pose a safety threat when children attempt to heat the fragrance material. In addition, having to keep matches or a butane lighter lying near the fragrance material for convenience can be visually unappealing. A further problem is that matches can be depleted or a butane lighter can be depleted of fuel.

Alternatively, heat from a light bulb has been used to heat a fragrance material. Some devices for heating a fragrance material use electricity. In either case, an electrical source such as an outlet needs to be nearby. Otherwise a line, such as an extension cord, needs to be run from the electrical source to the fragrance device which is not aesthetically pleasing and can cause a walkway hazard. This is especially true outdoors, which may also require that a light bulb be placed outdoors in some of the examples provided above. Furthermore, it requires that an outlet be taken up in order to operate the device causing inconvenience when electrical outlets are limited. In the case of battery powered devices, the battery can be depleted and replacing them can be costly.

Some devices use solar power, but only to provide electricity. They do not provide heat directly to the fragrance material, but rather supply electricity to a fan which disperses a scent. However, such devices create background noise which is undesirable. Furthermore, solar or battery operated fans are not applicable to fragrance materials that need heat directly applied in order to adequately release the fragrance entrapped therein to the surrounding atmosphere.

Therefore, what is needed is a device for heating a fragrance material that does not require an external flame such as from a match or a butane lighter. Furthermore, it is desirable that the device not require an external energy source such as electricity or a flame when heating the fragrance material. This would allow the device to be used outdoors as well as indoors and would be inexpensive to operate.

SUMMARY OF THE INVENTION

Accordingly, the invention is directed to a matchless, solar powered heating device having a base and a rotatable lens. The device utilizes solar energy to heat a volatile medium, which may be a liquid or embedded in another material. The device holds the medium or embedding material, and the rotatable lens is focused thereupon. The positioning of the rotatable lens thus enables the medium to be heated using solar energy, which vaporizes the volatile medium and releases it into the atmosphere in a gaseous form.

BRIEF DESCRIPTION OF THE DRAWINGS

These and other features and advantages will become more apparent from a detailed consideration of the invention when taken in conjunction with the drawings in which.

DETAILED DESCRIPTION OF THE INVENTION

Figure 1:
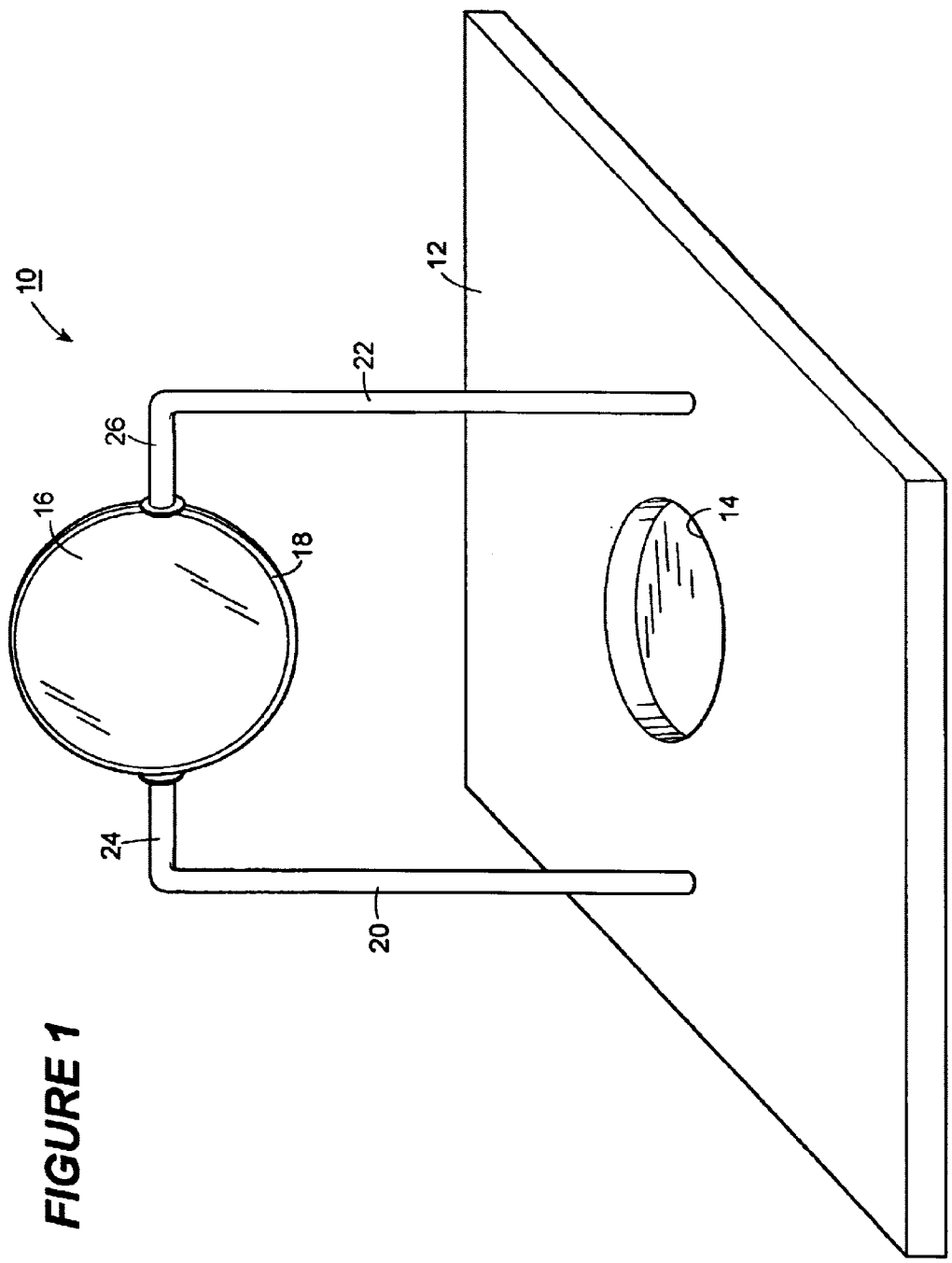
FIG. 1 is a perspective view of one embodiment of a device for releasing a fragrance.

Referring to the drawings, and with specific reference to FIG. 1, an apparatus for heating a fragrance material embedded with a volatile liquid to release a fragrance according to one embodiment of the invention is generally designated 10. The apparatus 10 includes a base 12 that may include a holder 14 for receiving a material upon or into which a volatile medium is adsorbed or absorbed, a fragrance liquid or other volatile liquid, gel, or other suitable material. As depicted in FIG. 1, the holder 14 is essentially a depression within the base 12 large enough for a fragrance material (e.g., a fragrance liquid) or a container to fit into. However, the holder 14 may also be a hole through the base, a spike or a nail, one or more pegs positioned around the medium, a raised rail, a raised ring or wall around the medium, a container attached to the base, an adhesive, a hook and loop fastener system, a combination of one or more of the above, or other suitable means may be employed to hold the above materials in place.

Figure 2A:
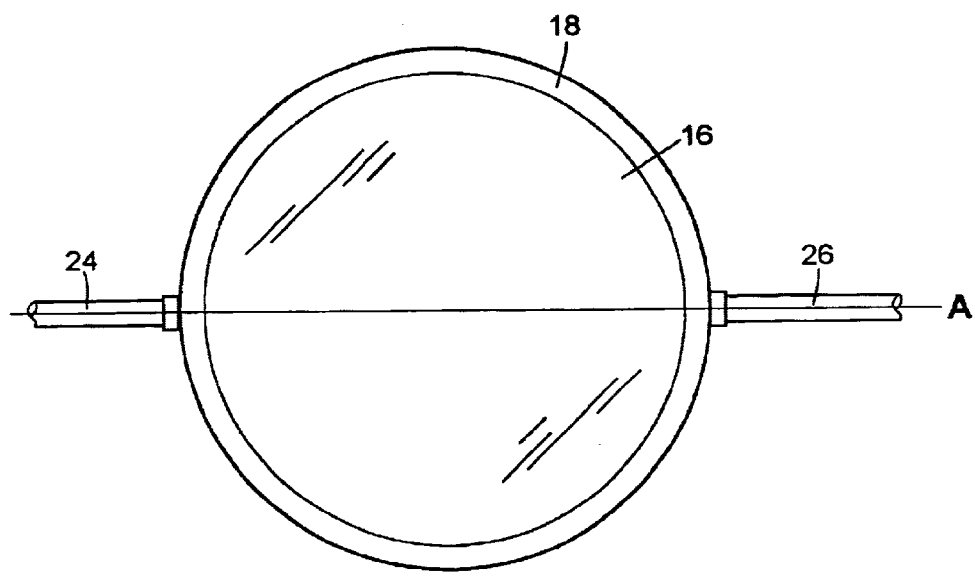
FIG. 2a is a partial front plan view of the embodiment shown in FIG. 1.
Figure 2B:
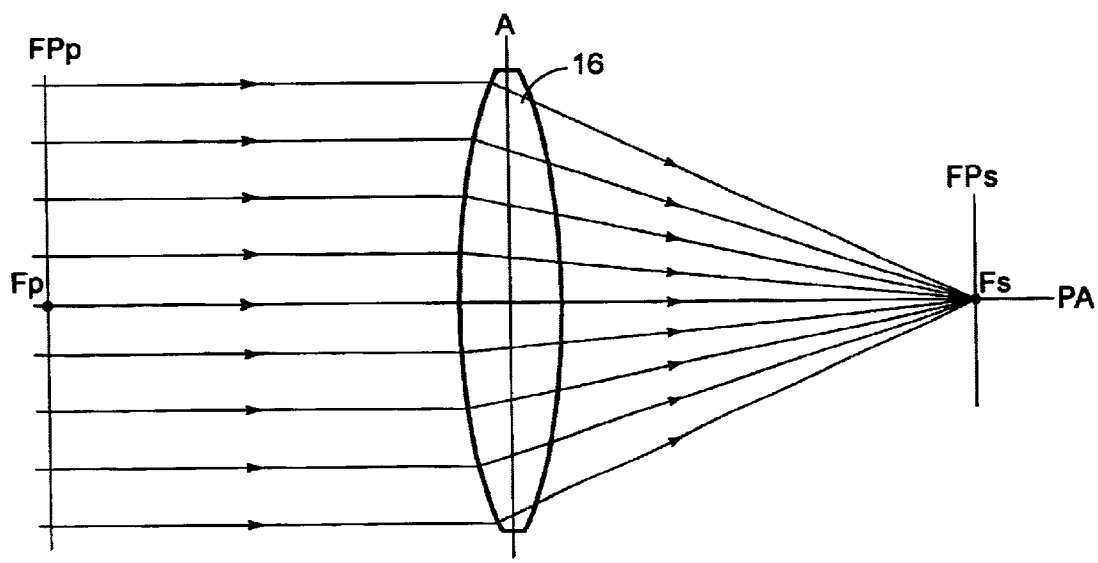
FIG. 2b is a schematic illustration of a preferred type of lens for use with the invention.

A rotatable lens 16 is positioned above the base 12. The lens may be similar to that of a magnifying glass. Any lens or combination of lenses that act as a converging lens (also known as a positive lens) with a focal length greater than zero is suitable. For example, referring to FIG. 2b, a single converging lens 16 is shown. The lens 16 has a primary focal point $F_P$ and a secondary focal point $F_S$ on a principal axis PA which respectively designates the primary focal plane $FP_P$ and the secondary focal plane $FP_S$. Ideally, the rotatable lens 16 rotates on a horizontal axis as shown in FIGS. 2a and 2b by a line A such that the lens 16 is rotated in the direction of the sun or an artificial light source (not shown). The axis A is essentially perpendicular to the principal axis PA and runs through the optical center of lens 16.

The rotatable lens 16 can be held in place by a ring 18, preferably made of metal, which is rotatably fixed to a stand. As shown in FIG. 1, the stand includes two vertical legs 20 and 22 attached to the base 12 on either side of the holder 14. The legs 20 and 22 extend upwardly from the base 12 with each leg terminating in a horizontal member 24 or 26, respectively, turning inwardly and facing one another. The combination of the leg 20 with the horizontal member 24 and the leg 22 with the horizontal member 26 may each be a single piece, thus forming two inverted L-shaped pieces. The inner ends of horizontal members 24 and 26 allow for rotatably mounting the ring 18 such that the lens 16 can rotate in the direction of the sun or artificial light source.

Figure 3:
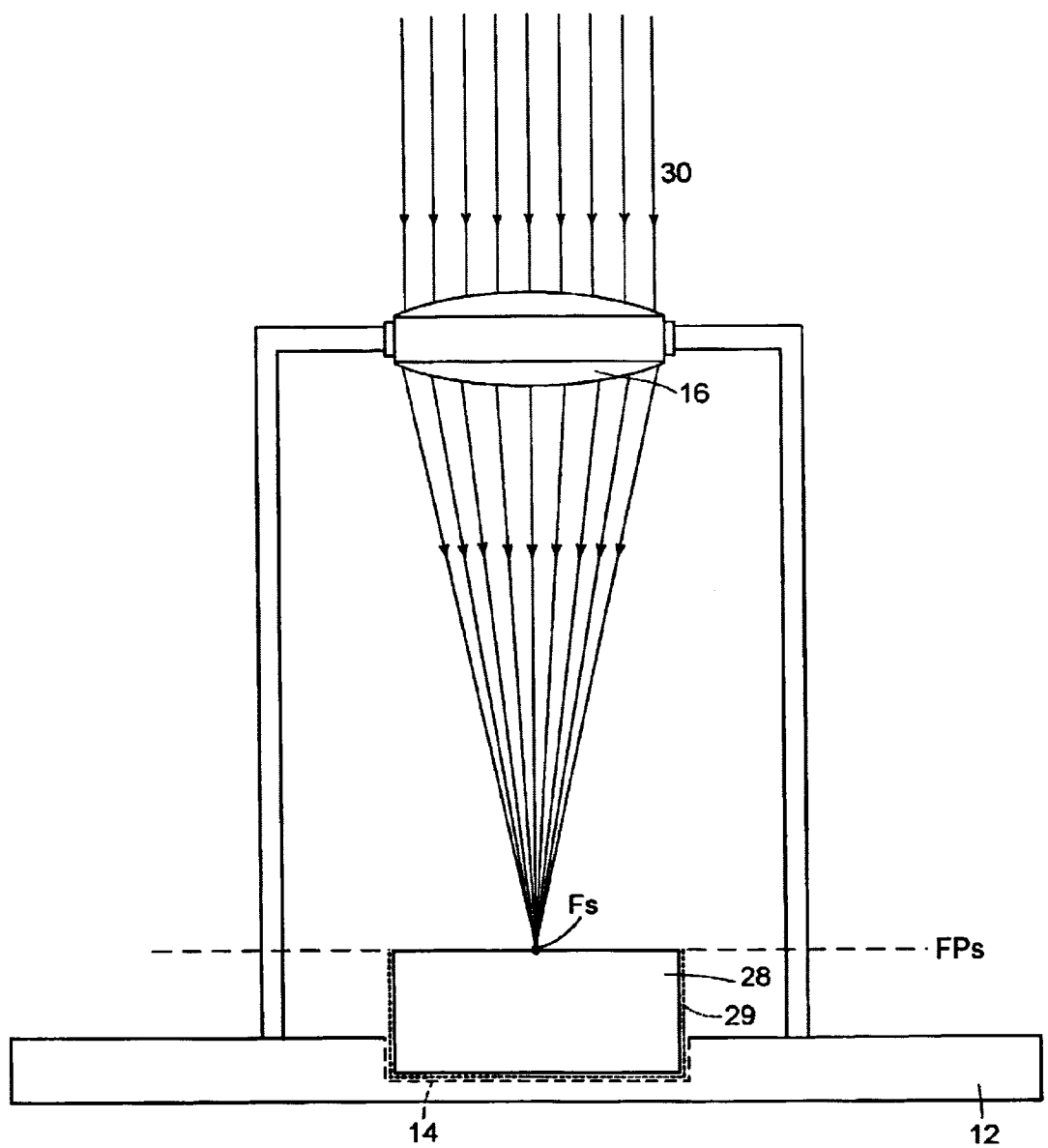
FIG. 3 is a side view of an embodiment of the invention heating a fragrance material with a partial cutaway of the base.

The apparatus as described above operates in a manner generally depicted in FIG. 3. A material 28 is positioned in the holder 14. The material 28 may be composed of starch, silica, zeolite, or any other particulate matter than can adsorb or absorb a volatile liquid. The material 28 may also be a solid, porous material wherein the volatile medium is adsorbed on the surface or absorbed by the material. Furthermore, the material 28 may be a liquid, such as a fragrance oil, in a separate container or dispersed in a vehicle or container, shown in phantom at 29, that sits under the rotatable lens 16. The fragrance itself may be of a variety of types such as an aesthetically pleasing fragrance, an insect repellent such as citronella, an insecticide, or another which is at least partly vaporized when heated.

The rotatable lens 16 is rotated in the direction of the sun (not pictured) to focus light rays (designated 30) on the material 28 in the holder 14. The material 28 and portion thereof to be heated is in the back focal plane $FP_S$ of the secondary focal point $F_S$ of the rotatable lens 16. In the case of a solid material or a liquid, the secondary focal point $F_S$ is preferably on the surface or just below the surface of the material 28. However, other methods may be used, such as heating the container in which the material 28 is encased thereby indirectly heating the material 28, for example when a volatile liquid is dispersed in a vehicle. The focusing of the light heats the material 28 to vaporize a volatile medium and/or release a fragrance infused in the material 28. In the case of a fragrance material, the fragrance is released into the surrounding atmosphere in a continuous manner creating a lasting fragranced ambience with the rotatable lens 16 rotating in the direction of the sun.

While the invention has been described with reference to specific examples, which are intended to be illustrative only, and not to be limiting of the invention, it will be apparent to those of ordinary skill in the art that changes, additions or deletions may be made to the disclosed embodiments without departing from the spirit and scope of the invention.

What is claimed is:

1. A device for heating a volatile medium, comprising:
   a base;
   a volatile medium holder containing a volatile medium; and
   a rotatable lens positioned above the base and independently rotatable with respect to the base in a direction of a source of light, the lens being positioned such that a focal point of the lens is focused on the volatile medium, the volatile medium being disposed between the base and the rotatable lens.

2. The device of claim 1, wherein the volatile medium is selected from the group consisting of a fragrance material and an insect repellent.

3. The device of claim 1, wherein the volatile medium is sorbed into or onto a particulate matter.

4. The device of claim 1, wherein the volatile medium is sorbed into or onto a porous material.

5. The device of claim 1, wherein the volatile medium is a liquid.

6. The device of claim 1, wherein the volatile medium holder is selected from the group consisting of a depression in the base, a hole in the base, a spike, one or more pegs, a raised rail, a raised ring, a wall, a container, an adhesive, and a hook and loop fastener system.

7. The device of claim 1, wherein the rotatable lens is selected from the group consisting of a magnifying glass and a converging lens.

8. The device of claim 1, wherein the rotatable lens rotates on an axis perpendicular to a principal axis of the rotatable lens.

9. The device of claim 1, further comprising a stand to hold the rotatable lens above the base.

10. The device of claim 9, wherein the rotatable lens is rotatably attached to the stand.

11. A device for heating a volatile medium, comprising:
    a base;
    means for positioning a volatile medium on the base; and
    a rotatable lens positioned above the base and independently rotatable with respect to the base in a direction of a source of light, the lens being positioned such that a focal point of the lens is focused on the volatile medium, the means for positioning the volatile medium being disposed between the base and the rotatable lens.

12. The device of claim 11, further including a volatile medium.

13. The device of claim 12, wherein the volatile medium is selected from the group consisting of a fragrance material and an insect repellent.

14. The device of claim 12, wherein the volatile medium is sorbed into or onto a particulate matter.

15. The device of claim 12, wherein the volatile medium is sorbed into or onto a porous material.

16. The device of claim 12, wherein the volatile medium is a liquid.

17. The device of claim 11, wherein the means for positioning is selected from the group consisting of a depression in the base, a hole in the base, a spike, a plurality of pegs, a raised rail, a raised ring, a wall, a container, an adhesive, and a hook and loop fastener system.

18. The device of claim 11, wherein the rotatable lens is selected from the group consisting of a magnifying glass and a converging lens.

19. The device of claim 11, wherein the rotatable lens rotates on an axis perpendicular to a principal axis of the rotatable lens.

20. The device of claim 11, further comprising a stand to hold the rotatable lens above the base.

21. The device of claim 20, wherein the rotatable lens is rotatably attached to the stand.

22. A device for heating a volatile medium, comprising:
    a base;
    a lens;
    a volatile medium holder being disposed on the base; and
    a leg connected to the base and extending upward therefrom, the leg further being connected to the lens to support the lens above the volatile medium holder, the lens being rotatably connected to the leg.

23. The device of claim 22, further including a volatile medium.

24. The device of claim 23, wherein the volatile medium is selected from the group consisting of a fragrance material and an insect repellent.

25. The device of claim 23, wherein the volatile medium is sorbed into or onto a particulate matter.

26. The device of claim 23, wherein the volatile medium is sorbed into or onto a porous material.

27. The device of claim 23, wherein the volatile medium is a liquid.

28. The device of claim 22, wherein the volatile medium holder is selected from the group consisting of a depression in the base, a hole in the base, a spike, one or more pegs, a raised rail, a raised ring, a wall, a container, an adhesive, and a hook and loop fastener system.

29. The device of claim 22, wherein the rotatable lens is selected from the group consisting of a magnifying glass and a converging lens.

30. The device of claim 22, wherein the rotatable lens rotates on an axis perpendicular to the primary axis of the rotatable lens.

31. The device of claim 22, wherein the leg comprises a first leg and a second leg, the lens being rotatably connected to the first leg and the second leg.

* * * * *